| United States Patent [19] | [11] 4,005,132 |
|---|---|
| Koster et al. | [45] Jan. 25, 1977 |

[54] PROCESS FOR REACTING TRIALKYL BORANES WITH COMPOUNDS CONTAINING PROTONS

[75] Inventors: Roland Koster, Mulheim (Ruhr); Hans Bellut, Wanne-Eickel, both of Germany

[73] Assignee: Studiengesellschaft Kohle m.b.H., Mulheim (Ruhr), Germany

[22] Filed: Oct. 12, 1972

[21] Appl. No.: 297,146

[30] Foreign Application Priority Data

Oct. 14, 1971 Germany .......................... 2151233

[52] U.S. Cl. .................................. 260/502.3; 536/4; 260/340.6; 260/343.7; 260/458 R; 260/462 C; 260/551 B; 423/491; 423/551; 23/230 R; 252/408

[51] Int. Cl.² .......................................... C07F 5/02

[58] Field of Search ......... 260/502.3, 462 C, 551 B

[56] References Cited

UNITED STATES PATENTS

| 3,030,406 | 4/1962 | Washburn et al. ............. 260/502.3 |
| 3,072,715 | 1/1963 | Willcockson ................... 260/502.3 |
| 3,335,175 | 8/1967 | Pearson ......................... 260/502.3 |

OTHER PUBLICATIONS

Muetterties, The Chemistry of Boron and Its Compounds, John Wiley & Sons, N.Y. pp. 582 to 585 (1967).
Steinberg et al., Boron Chemistry, vol. 1, The Macmillan Co. N.Y. pp. 371-372 (1964).

*Primary Examiner*—Helen M. S. Sneed
*Attorney, Agent, or Firm*—Burgess, Dinklage & Sprung

[57] ABSTRACT

Trialkyl boranes are reacted with compounds containing protons in the presence of catalytic amounts of carboxylic acid derivatives, especially derivatives of t-alkyl carboxylic acids, thereby highly increasing the rate of protolyses of trialkyl boranes. These reactions may, for example, be utilized for the borylation of H-acidic compounds or for the dehydration of salts.

19 Claims, No Drawings

PROCESS FOR REACTING TRIALKYL BORANES WITH COMPOUNDS CONTAINING PROTONS

This invention relates to a process for reacting trialkyl boranes with compounds containing protons.

Trialkyl boranes $BR_3$ (R = alkyl) are known to react with H-acidic compounds H-X according to the general equation $$R_3B + H-X \longrightarrow R_2B-X + RH$$

to form alkane RH and O- or N-dialkyl boryl derivatives. The reaction rates vary depending upon R and X. While the reactions of the trialkyl boranes with carboxylic acids (X = O-acyl) generally occur at as low as room temperature, it is necessary to heat at 160° to 170° C when using alcohols (X = O-alkyl) or phenols (X = O-aryl), at 170° to 200° C. when using dialkyl amines (X = N-alkyl$_2$) and at about 100° C. when using alkane- and benzene sulfonic acids (X = OSO$_2$alkyl, O-SO$_2$aryl). However, some of the functional groups may be reduced in this reaction by the BH bonds formed intermediately.

It has now been found that the protolysis of trialkyl boranes can be highly accelerated by small amounts of carboxylic acid derivatives. Above all, the derivatives of t-alkyl carboxylic acids such as pivalic acid or adamantane-1-carboxylic acid have been found to be particularly useful catalysts of the protolysis of trialkyl boranes.

Triethyl borane to which 0.1 to 1 mole percent of pivalic acid are added reacts with water or with alcohols at a high rate and quantitatively at as low as room temperature with cleavage of an ethyl group as ethane:

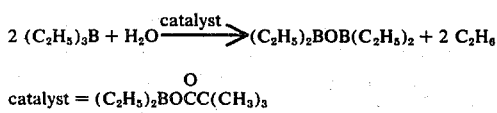

$$2 (C_2H_5)_3B + H_2O \xrightarrow{\text{catalyst}} (C_2H_5)_2BOB(C_2H_5)_2 + 2 C_2H_6$$

$$\text{catalyst} = (C_2H_5)_2BO\overset{O}{\overset{\|}{C}}C(CH_3)_3$$

For example, when using triethyl borane and adding diethyl boryl pivalate, the water of cristallization and constitution of many metal salt hydrates can be determined in a very simple analytical manner. The amount of ethane evolved gives an accurate measure for the water content of the metal salts. The ethane is determined volumetrically.

Since the salts remain almost always undissolved on dehydration (see Table 1), they can also be readily recovered preparatively in anhydrous form. In contrast to some of the known dehydration processes, the total water of hydration is removed in accordance with the invention.

Dehydration by prior art processes, e.g. by simple heating and by azeotropic distillation gives rise to impure compounds in many cases due to hydrolysis, e.g. in case of metal halides. Other known processes of dehydration by means of chemical reactions, e.g. by means of thionyl chloride, often do not furnish uniform dehydrated salts due to the reactivity of the dehydrating agent or of its reaction products. These disadvantages are avoided when using activated triethyl borane. The borane reacts under very mild conditions. In most cases, it is not necessary to heat to temperatures in excess of 50°C. Triethyl borane and the materials formed on dehydration such as tetraethyl diboron oxide and ethane are inert to most metal salts under the conditions of dehydration. Therefore, it is readily possible to recover the anhydrous salts in substantially quantitative yields and in high purity. The salts which are generally completely insoluble in the liquid dehydration mixture are, for example, isolated after filtration and washing with an aliphatic hydrocarbon such as pentane.

After addition of an alkyl or aryl carboxylic acid, especially pivalic acid, trimethyl, tripropyl, triisopropyl and triisobutyl boranes similar to triethyl borane react more rapidly with water than without the addition. However, the catalyzed hydrolyses of the trialkyl boranes $BR_3$ proceed at differen rates, viz. for $$R = C_2H_5 > C_3H_7 >> CH(CH_3)_2 >> CH_2CH(CH_3)_2.$$

This is also true of the reactions of trialkyl boranes with alcohols or phenols. Up to about 100° C., only one alkyl group of the trialkyl boranes is split off as alkane in all cases.

Alkyloxy and aryloxy dialkyl boranes can be readily produced by means of the catalyzed protolysis. In this reaction, the alkyl groups may also contain functional groups such as C=C- or C≡C- or $NO_2$ groups.

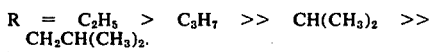

$$R_3B + HOR' \xrightarrow{\text{catalyst}} R_2BOR' + HR$$

R = Et, Pr, iPr, iBu    R' = alkyl, aryl

After addition of small amounts of pivalic acid, alkane and benzene sulfonic acids also react smoothly with trialkyl boranes at as low as room temperature to form dialkyl boryl alkane and -benzene sulfonates, respectively in high yields:

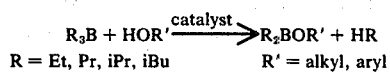

$$R_3B + HOSO_2R' \xrightarrow{\text{catalyst}} R_2BOSO_2R' + RH$$

R = Et, Pr, iPr, iBu    R' = alkyl, phenyl

Triethyl borane reacts with oxygen-containing acids such as concentrated sulfuric acid, phosphoric acids or boric acid and also with iodic acid with cleavage of ethane in the presence of diethyl boryl pivalate to form the corresponding diethyl boryl esters, e.g.

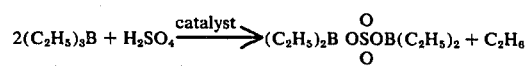

$$2(C_2H_5)_3B + H_2SO_4 \xrightarrow{\text{catalyst}} (C_2H_5)_2B\,\overset{O}{\underset{O}{\text{OSOB}}}(C_2H_5)_2 + C_2H_6$$

Without the use of a catalyst, the reactions are very slow and do not give uniform products due to secondary and consecutive reactions.

The diethyl borylation of polyhydroxy compounds also proceeds particularly smoothly with the addition of pivalic acid. Therefore, the content of hydroxyl groups of compounds which are dissolved but also of compounds which are not dissolved such as starch and cellulose can be determined exactly by this analytical method. The introduction of O-diethyl boryl protective groups into sugar and sugar derivatives is of commercial interest. The perdiethylborylated monosaccharides and their derivatives which are very readily soluble in hydrocarbons include, for example, 1,2,3,4,5-pentakis(diethylboryl)-D-(+)-glucose (b.p. = 136°

C./0.001 mm. Hg), 2,3,4,6-tetrakis(diethylboryl)-α-methyl-D-(+)-glucoside (b.p. = 130° C./0.001 mm. Hg), 2,3,5,6-tetrakis- (diethylboryl)-L-(+)-ascorbic acid, and can be subjected to vacuum distillation without decomposition.

Furthermore, the process according to the invention can be advantageously used for the catalytic borylation of dextrines. It is achieved by this process that these products become soluble in organic solvents.

The diethyl boryl groups can be split off with methanol in a very mild and preserving manner and quantitatively.

The reactions of trialkyl boranes with specific enolizable carbonyl compounds can also be highly accelerated by the addition of carboxylic acids or esters thereof, especially by the addition of pivalic acid esters $(CH_3)_3CCOOR$ wherein R is $BR_2$ or

Depending upon the organic radicals of the $R''_2CO$ compounds, either vinyloxy dialkyl boranes in yields up to 98% or condensation products of the carbonyl compounds are obtained.

For example, when heating diethyl ketone and triethyl borane to 50° to 70° C. in the presence of diethyl boryl pivalate, 98% of ethane and only 2% of ethylene are formed. 82 Percent of 3-diethyl-boryl-oxy-2-pentene are isolated.

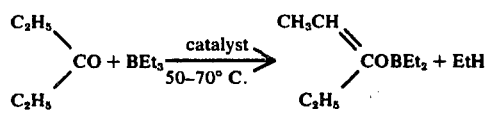

The boron-containing products are 3-diethyl-boryl-oxypentene and 3-diethylboryl-oxy-2-pentane, the latter having been formed by reduction:

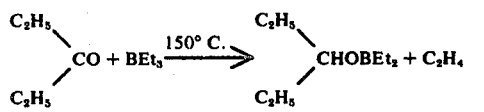

Diethylboryl cycloenolates and substantially no reaction products are also formed from cycloketones having seven and more ring members with triethyl borane under conditions of catalysis. Cyclododecanone exclusively furnishes a mixture of the two cis/trans-isomeric diethylboryl-oxycyclododecenes. On the other hand, only 70% of diethylboryl-oxy-cis-cycloheptene in addition to 30 % of $C_{14}H_{22}O$-ketone which is a condensation product of two ketone molecules are produced from cycloheptanone.

The introduction of dialkyl boryl groups can be highly accelerated by means of trialkyl boranes also in case of a great number of NH-compounds in the presence of alkyl carboxylic acid derivatives. Ammonia, primary and secondary amines as well as pyrrole and pyrrole bases react with cleavage of alkane to form N-dialkyl-borylated derivatives:

Hydrazines can also be dialkylborylated in this manner. Furthermore carboxamides and carboxylic acid hydrazides react under conditions which are substantially milder than those used without a catalyst. Aldo- and ketophenylhydrazones and phenylosazones can also be reacted with the activated trialkyl boranes under mild conditions. Phenyl osazones such as glyoxal phenyl osazone react with triethyl borane with cleavage of 2 moles of ethane to form deep colored compounds. In general, a temperature of 50° to 80° C. is sufficient for the reactions with the NH-compounds. Dialkylamines require heating to more than 100° C. to ensure rapid splitting-off of gas.

The rate of reactions of SH-compounds with trialkyl boranes in the presence of the carboxylic acid catalysts is also markedly higher than without the addition. Thus, when reacting hydrogen sulfide with triethyl borane after the addition of diethyl boryl pivalate, a temperature of only about 50° C. is necessary while heating to more than 150° C. is necessary without a catalyst to achieve a comparatively high reaction rate. Thiols are known to react readily with trialkyl boranes while splitting-off alkane to form alkylthio-dialkyl boranes.

Finally, the rates of the reactions of hydrogen halides with trialkyl boranes can also be increased by alkyl caboxylic acid esters, especially by dialkyl boryl esters. This is true above all of reactions of hydrogen chloride with trialkyl boranes.

In accordance with the invention, the process may be carried out in the presence of solvents. However, it is preferred to operate without additional solvents. Suitable solvents include trialkyl boranes, e.g. boron trialkyls, aliphatic and aromatic hydrocarbons, dialkyl ethers, diethylene glycol, dimethyl ether or dioxane.

A temperature ranging between 0° and 60° C. is preferred for the reactions to be carried out according to the invention. In certain cases a temperature up to 100° C. is necessary. The following examples illustrate the invention.

EXAMPLE 1

Triethyl borane and water:

a. Without a catalyst: 5 ml of triethyl borane are heated with 80 mg. (4.45 millimoles) of $H_2O$ to a temperature above 80° C. After about 1 hour, splitting-off of gas is terminated. There are obtained 192 Nml (normal milliliters) of ethane corresponding to 96.5% of the theory.

b. With a catalyst: To 5 ml of triethyl borane to which about 50 mg. of pivalic acid had been added are added 80 mg. (4.45 millimoles) of $H_2O$ at room temperature. Vigorous evolution of gas occurs immediately and the temperature rises to about 35° C. Within 5 minutes are obtained 197 Nml of ethane corresponding to 100% of the theory.

EXAMPLE 2

Determination of water in dioxane 26.67 Grams of dioxane are mixed with about 5 ml of activated (+ about 100 mg. of pivalic acid) triethyl borane. When heated to 50° to 60° C., 53.6 Nml of ethane corresponding to 1.195 millimoles of $H_2O$ = 0.84%o of $H_2O$ are evolved within about 5 minutes.

EXAMPLE 3

Dehydration of $Na_2SO_4 \cdot 10\ H_2O$

In about 4 hours, 20 g. (0.062 moles) of sodium sulfate decahydrate are added in portions with stirring to 133 g. (1.365 moles) of triethyl borane to which 1 ml of diethyl boryl pivalate had been added. The temperature rises. Above 35° C., vigorous evolution of gas occurs. While the temperature further increases to about 70° C., 27.8 Nl (normal liters) of ethane (101%) are obtained. Thereafter the liquid is separated from the solid salt by filtration and the salt is extracted for 10 hours with hexane in a Soxhlet extractor. After drying under a high vacuum ($10^{-3}$ mm. Hg), 8.5 g. (96%) of pure $Na_2SO_4$ are recovered.

EXAMPLE 4

Dehydration of $MnCl_2 \cdot 4H_2O$

When adding 5 g. (25.3 millimoles) of manganese dichloride tetrahydrate in portions to 29.4 g. (300 millimoles) of triethyl borane to which 1 ml of diethyl boryl pivalate had been added, 2.74 normal liters (100%) of ethane are obtained after about 3 hours at 60° C. After filtration and drying under vacuum at room temperature, 3.1 g. (97%) of pure $MnCl_2$ are recovered.

EXAMPLE 5

The procedure described in Examples 3 and 4 is followed using various hydrous salts. The results are given in Table 1.

Table 1

$H_2O$ Determination[a] of metal salt hydrates with triethyl borane with the addition of diethyl boryl pivalate

| Salt hydrate[b] | calc'd[b] | per cent $H_2O$[c] found[d] (with catalyst) | found[e] (without catalyst) | $\frac{found}{calculated} \times 10^2$ with catalyst[d] | without catalyst[e] |
|---|---|---|---|---|---|
| $Li_2SO \cdot H_2O$ | 14.08 | 13.66 | 11.85 | 97.2 | 84.2 |
| $Na_2S \cdot 9H_2O$ | 67.51 | 64.94 | 11.60 | 96.4 | 17.2 |
| $Na_2S_2O_3 \cdot 3H_2O$ | 36.29 | 36.70 | 33.58 | 101.1 | 92.6 |
| $Na_3PO_4 \cdot 12H_2O$ | 56.87 | 57.64 | 7.54 | 101.1 | 13.2 |
| $Na_2Cr_2O_7 \cdot 2H_2O$ | 12.09 | 12.18 | 12.29 | 100.8 | 101.7 |
| $NaVO_3 \cdot 4H_2O$ | 37.15 | 38.98 | 24.34 | 104.8 | 65.6 |
| $MgSiF_6 \cdot 6H_2O$ | 39.38 | 39.51 | 16.48 | 100.1 | 41.8 |
| $CaCl_2 \cdot 4H_2O$ | 39.37 | 39.70 | 28.91 | 100.9 | 73.5 |
| $Ca(NO_3)_2 \cdot 4H_2O$ | 30.51 | 31.43 | 27.61 | 102.9 | 90.4 |
| $Ca(SCN)_2 \cdot 4H_2O$ | 31.56 | 31.79 | 29.96 | 100.5 | 95.5 |
| $MnCl_2 \cdot 4H_2O$ | 36.41 | 37.40 | 32.46 | 102.4 | 90 |
| $FeCl_2 \cdot 4H_2O$ | 36.25 | 36.17 | 34.10 | 100 | 94.6 | a) Volumetric determination of the evolved ethane. b) Commercially available salts having water contents specified by suppliers; see (d). c) In the presence of a catalyst, the determinations can be carried out substantially more rapidly and at a lower temperature (20 to 50° C.) (cf. (d) and (e)). d) Evolution of ethane with spontaneous heating is generally terminated after 5 minutes. This is followed by short-time heating to the boiling point. The values are reproducible. Greater deviations from the calculated $H_2O$ content are due to impurity of the commercially available salt hydrates. e) Quantity of ethane obtained after heating for 1 to 2 hours in boiling triethyl borane.

EXAMPLE 6

The procedure described in Examples 3 and 4 was followed. The results are shown in Table 2.

Table 2

Determination of OH groups of hydroxy compounds[a] with activated triethyl borane[b]

| OH compound | Weight of sample millimoles | Temp.[c] ° C. | Duration of $C_2H_6$ evolution | Ethane found[d] Mmoles | $\frac{found}{calculated} \times 100$ |
|---|---|---|---|---|---|
| 1-Octanol | 4.31 | 20–40 | 15' | 4.27 | 99 |
| 2-Ethyl hexanol | 5.72 | 10–35 | 4' | 5.6 | 98 |
|  | 2.93 | 20–40 | 2' | 2.85 | 97 |
| 3,3-Dimethyl propanol (Neopentanol) | 5.90 | 20–65 | 45'' | 5.94 | 101 |
| Crotyl alcohol | 4.35 | 20–60 | 15'' | 4.4 | 101 |
| 1-Butyn-3-ol | 3.1 | 20–50 | 15'' | 3.3 | 106 |
| Cinnamic alcohol | 3.45 | 20–50 | 20'' | 3.46 | 100 |
| 2-Bromoethanol | 7.52 | 20–40 | 10'' | 7.89 | 105 |
| 2,2,2-Trifluoroethanol | 3.876 | 20–50 | 10'' | 3.67 | 95 |
| Citric acid triethyl ester | 2.45 | 20–40 | 1' | 2.57 | 105 |
| Phenol | 5.69 | 20–50 | 30'' | 5.4 | 96 |
| Hydroquinone | 1.7 | 20–50 | 30'' | 3.54 | 104 |
| Resorcinol | 1.75 | 20–50 | 30'' | 3.6 | 103 |
| 2.6-Di-t-butyl phenol | 2.15 | 20–40 | 10'' | 2.13 | 99 | a) Commercially available compounds which had not been subjected to further special purification. b) Activated by adding about 100 mg. of pivalic acid to 5 ml of triethyl borane c) Approximate temperature interval by heat of reaction. d) Deviations from 100% are due to impurities in the compounds; cf. (a).

EXAMPLE 7

1,2,3,4,5-Pentakis-diethyl-boryl-D(+)-glucose

To 14 g. (78 Mmoles) of D(+)-glucose melting at 145° C. (dried under vacuum at 95° C.[bath]) in 60 ml of absolute heptane are added dropwise with stirring within about 3 hours 40 g. (410 Mmoles) of triethyl borane activated with about 200 mg. of pivalic acid. Evolution of gas starts at room temperature. The temperature in the mixture rises to about 50° C. After complete dissolution and evolution of 8.81 normal liters (100%) of pure ethane and withdrawal of the triethyl borane and heptane, 41.8 g. (100%) of per-O-diethyl-borylated glucose are obtained as a colorless clear liquid. Found, 6.94% B (on C); calculated, 6.94% B (on C). Under high vacuum, the compound can be distilled substantially without a residue at 136° C./10$^-$mm. Hg as a colorless and readily mobile liquid without decomposition.

Methanolysis: A precipitate is immediately obtained from 5.65 g. (10.8 Mmoles) per-O-diethyl-borylated glucose after admixture of about 60 ml. of methanol. Methoxy-diethyl borane and methanol are distilled off under atmospheric pressure to give 1.9 g. (97%) of pure (thin layer chromatography) glucose having a melting point of 145° C.

EXAMPLE 8

2.3.5.6-Tetrakis-diethylboryl-L(+)-ascorbic acid

To a suspension of 11.8g. (67 Mmoles) of ascorbic acid (vitamin C) in about 50 ml of heptane are added dropwise with stirring within 3 hours at room temperature 28.4 g. (280Mmoles) of triethyl borane mixed with 0.2 ml of diethyl boryl pivalate. While gas is vigorously evolved (a total of 5.97 normal liters (100%) of pure ethane), the temperature rises to about 40° C. After further heating to about 50° C. for 30 minutes, a colorless clear solution is obtained. The solvent and excess triethyl borane are distilled under vacuum to give 30.3 g. (101%) of a colorless viscous compound having a boiling point of 156° C./10$^{-3}$ mm.Hg. Found, 6.38% B (on C); calculated, 6.44% B (on C).

EXAMPLE 9

2,3,4,6,1',3',4',6'-Octakis-diethylboryl sucrose

A completely clear and colorless solution is obtained when adding dropwise within 2.5 hours 36 g. (368 Mmoles) of triethyl borane mixed with 0.1 ml of diethyl boryl pivalate to 14.7 g. (43 Mmoles) of surcrose (cane sugar) (= alpha-D-glucopyranosido-$\beta$-D-fructofuranoside) in about 70 ml. heptane at 50° to 65° C. with vigorous evolution of gas (7.65 normal liters of ethane (99%)). After removal of triethyl borane and heptane under vacuum, 38 g. (100%) of a colorless viscous compound remain. Found, 6.4% B (on C); calculated, 6.50 B (on C).

EXAMPLE 10

The procedure of Examples 7 to 9 is followed. The results are given in Table 3.

Table 3

H$_{OH}$ Determination[a] in sugars and sugar derivatives with activated triethyl borane[b]

| Compound | Reaction conditions | | | | H$_2$O found $\frac{found}{calculated} \times 10^2$ | |
|---|---|---|---|---|---|---|
| | cat.[b] | t$_{max}$ °C | time[c] (min.) | cat.: | − | + |
| D(+) xylose | − | 60 | 15 | | 102 | |
| | + | 20 | 1 | | | 101 |
| L(+) arabinose | − | 30 | 10 | | 99.2 | |
| | + | 30 | 1 | | | 101 |
| D(+) glucose | − | 70 | 30 | | 98.9 | |
| | + | 25 | 1 | | | 99 |
| D(−) fructose | − | 60 | 15 | | 101 | |
| | + | 40 | 2 | | | 101 |
| Maltose | − | 70 | 25 | | 102 | |
| | + | 25 | 1 | | | 106 |
| Raffinose hydrate | − | 70 | 20 | | 100.5 | |
| | + | 30 | 5 | | | 99 |
| Cellulose | + | 60 | 80 | | | 101 |
| 4,6-0-Benzylidene-D-glucopyranose | − | 80 | 30 | | 98 | |
| | + | 25 | 5 | | | 102 |
| L(+) ascorbic acid | − | 80 | 120 | | 101 | |
| | + | 30 | 60 | | | 98 |
| $\beta$-Methyl-3-deoxy-3-aminogluco-pyranoside | − | 80 | 120 | | 82 | |
| | + | 25 | 7 | | | 101 |

[a]Volumetric determination of ethane evolved.
[b]Catalyst: diethyl boryl pivalate
[c]Duration of ethane evolution (room temperature to t$_{max}$)

EXAMPLE 11

Borylation of Cellulose

To 2.7 g. (16.65 Mmoles) of cellulose in 40 ml. of heptane are added dropwise within 70 minutes with stirring at 60° to 70° C (bath) 6.3 g. (64.3 Mmoles) of triethyl borane mixed with 0.1 ml of diethyl boryl pivalate. Thereafter about 700 Nml of ethane evolved. Heating to 70° to 80° C. for 1.5 hours gives a total of 1135 Nml (101%) of ethane. The liquid is removed by filtration from the voluminous white solid substance. After washing for three times with pentane and drying under vacuum, 5.85 g. (96%) of per-O-diethyl-borylated cellulose are obtained Found, 5.84% B (on C) which is insoluble in aliphatic and aromatic hydrocarbons and in carbon tetrachloride.

EXAMPLE 12

Bis(diethylboryl)sulfate

To 79 g. (806 Mmoles) of triethyl borane mixed with about 0.5 ml of diethyl boryl pivalate are added dropwise within about 2 hours 15.6 g. of 98% sulfuric acid (corresponding to 345 mg.–atoms of H). While increasing the temperature from room temperature to about 50° C., there are obtained 7.32 normal liters (327 Mmoles) of ethane and 84.2 g. of a clear pink liquid from which a small amount of a dark solid substance precipitates. After 51 g. of a mixture (triethyl borane and tetraethyl diboron oxide) boiling up to 25° C./15 mm.Hg, 30 g. (82%) of bis(diethylboryl)sulfate having a boiling point of 66° to 67° C./0.001 mm. Hg distil under vacuum. The amount of residue is 1.9 g.

EXAMPLE 13

3-Diethylboryloxy-2-pentene

To 49 g. (0.5 moles) of boiling triethyl borane mixed with 2 ml of diethyl boryl pivalate were added dropwise at 40° to 60° C. within 80 minutes 43 grams (0.5 moles) of 3-pentanone. During the addition, gas is evolved. Heating is continued for about 15 hours at about 100° C. to give 12 normal liters of gas with (MS) 98% of $C_2H_6$ and 2% of $C_2H_4$. After having collected 9 g. of first runnings boiling up to 44° C./15 mm. Hg, 61 g. (82%) of colorless isomer-free 3-diethyl-boryl-oxy-2-pentene having a boiling point of 57° to 59° C./15 mm. Hg are obtained under vacuum with almost no residue.

I.R. spectrum (neat): 1680 cm$^{-1}$($_{C=C}$).
$^1$H-NMR spectrum (neat): = 5.41 (vinyl H)

EXAMPLE 14 t-Butylamino-diethyl borane

A mixture of 14.6 g. (0.2 moles) of t-butylamine and about 30 g. (0.3 moles) of triethyl borane after addition of about 1 g. of diethyl boryl pivalate is heated to 60° to 80° C. with stirring. Within 2.5 hours, 6.2 normal liters (92%) of ethane are evolved. Distillation under vacuum gives 24 g. (85%) of pure t-butylamino-diethyl borane boiling at 45° C./18 mm. Hg after having collected unconsumed triethyl borane. The residue weighs about 1 g.

In an analogous manner, sec. butylamino-diethyl borane having a boiling point of 48° C./18 mm. Hg is obtained in a 90% yield from sec. butylamine and activated triethyl borane.

EXAMPLE 15

Anilino-diisobutyl borane

A mixture is prepared from 18.4 g. (0.1 moles) of triisobutylborane and 0.5 g. pivalic acid and heated to 70° C. Within 3 hours, 9.4 g. (0.1 moles) of aniline are added dropwise and then heating is continued for 2.5 hours to a maximum of 80° C. 1890 Nl (84.4 Mmoles) of isobutane are evolved. After having collected a small amount of first runnings of b.p. up to 28° C./0.1 mm. Hg, 18.4 g. (84.8%) of colorlos anilinodi-isobutyl borane of b.p. 49°–51° C./0.1 mm. Hg and 1.1 g. of residue are obtained.

EXAMPLE 16

The catalytic activity of pivalic acid derivatives in the alcoholysis of triethyl borane[a] is compared. The results are given in Table 4.

Table 4

| Pivalic acid derivative $(CH_3)_3C-X$ | Alcohol | Temp.[b] ° C. | Evolution of $C_2H_6$ (minutes) | Yield of isolated diethyl-butyl derivative |
|---|---|---|---|---|
| X = CONEt$_2$ | ethanol | 86–92 | 80 | 86 |
| COOC$_6$H$_5$ | 1-butanol | 84–87 | 480 | 94 |
| CONEt$_2$ | allyl alcohol | 84 | 80 | 94 |
| COOCH$_2$C(CH$_3$)$_3$ | 1-buten-3-ol | 80–90 | 40 | 96 |
| COOCH$_3$ | 1-buten-3-ol | 80–90 | 90 | 93 |
| CN | 1-buten-3-ol | 85 | 180 | 78 |
| CONEt$_2$ | 1-butyn-3-ol | 90–100 | 90 | 79 |
| COOCH$_3$ | 2-methyl-2-butanol | 100 | 90 | 94.4 |

[a]Triethyl borane/used in excess.
[b]Necessary temperature for quantitative evolution of ethane.

EXAMPLE 17

The catalytic activities of carboxylic acid diethylboryl esters in the reaction of triethyl borane[a] with 1-octanol[b] were compared. The results are given in Table 5.

Table 5

| Carboxylic acid diethylboryl ester[c] | Temperature interval[d] | Approx. duration of $C_2H_6$ evolution, min. | Amount of $C_2H_6$ recovered, % |
|---|---|---|---|
| $\overset{O}{R-C-OBET_2}$ | | | |
| R = CH$_3$(CH$_2$)$_5$— | 37–53 | 1 | 93.6 |
| CH$_3$CH(CH$_3$)— | 28–55 | 1.5 | 97.9 |
| (CH$_3$)$_3$C— | 20–56 | 0.25 | 99.5 |
| (adamantyl) | 24–56 | 1 | 100.5 |
| C$_6$H$_5$CH=CH— | 23–48 | 12 | 103.8 |

Table 5-continued

| Carboxylic acid diethylboryl ester[c] | Temperature interval[d] | Approx. duration of $C_2H_6$ evolution, min. | Amount of $C_2H_6$ recovered, % |
|---|---|---|---|
|  | 29–53 | 8 | 100.8 |
| $CH_3CHBr-$ | 25–35 | 33 | 98.6 |
| $CH_2BrCH_2-$ | 25–40 | 15 | 98.6 |
| $P(Et_2BNH)-C_6H_4$ | 23–37 | 7 | 97.9 |

[a] Triethyl borane used in excess.
[b] 1-Octanol charged (3 to 4 moles).
[c] Addition of 2 drops of catalyst in each case.
[d] Catalyst added at room temperature; the temperature interval is given in which gas evolution was vigorous (spontaneous heating).

EXAMPLE 18

Per-O-diethylboryl-cyclohepta-amylose (I)

To 180 g. (1.84 moles) of triethyl borane to which 0.2 ml of diethyl boryl pivalate had been given are added within 9 hours 29.4 g. (25.9 millimoles) of cycloheptaamylose (β-cyclodextrine) at 85° C. (bath). There are evolved 12.62 Nl (104%) of ethane (MS). After separation of excess triethyl borane, 62.7 g. (94.5%) of (I) are obtained as a colorless crystalline compound which is soluble in aliphatic and aromatic hydrocarbons and in carbon tetrachloride. Decomposition of the compound begins at 141° C with evolution of triethyl borane. -OH absorption is not detectable in the IR spectrum.

$C_{126}H_{259}B_{21}O_{35}$ (2561.5) Calculated: B 8.86 B (on C) 5.91; Found: 8.91 5.90.

What is claimed is:

1. A process for reacting trialkyl borane with a compound containing a proton for protolysis of the trialkyl borane and said compound involving said proton, said compound being a compound having the proton bonded to 0 or N, with the proviso that when the proton is bonded to the residue by 0, the residue is other than acyl, an HS compound wherein H in said HS is said proton, or hydrogen halide, wherein the hydrogen in said hydrogen halide is said proton, which comprises carrying out the reaction in the presence of catalytic amount of a carboxylic acid derivative which is a catalyst for the reaction.

2. The process according to claim 1 wherein said carboxylic acid derivative is a derivative of a t-alkyl carboxylic acid.

3. The process according to claim 1 wherein said reaction is carried out in the presence of a catalytic amount of a dialkyl boryl ester of a t-alkyl carboxylic acid.

4. Process according to claim 1, wherein said carboxylic acid derivative is a dialkyl boryl ester of a carboxylic acid.

5. Process according to claim 4, wherein said dialkyl boryl ester is a dialkyl boryl ester of pivalic acid.

6. Process according to claim 4, wherein said dialkyl boryl ester is a dialkyl boryl ester of adamantane-1-carboxylic acid.

7. Process according to claim 5, wherein said trialkyl borane is triethyl borane and the dialkyl boryl ester of pivalic acid is diethyl boryl pivalate formed by addition of 0.1 to 1 mole percent, based on the triethyl borane, of pivalic acid.

8. Process according to claim 7, wherein said compound is water, an alcohol, an acid or an amine.

9. Process according to claim 8, wherein said compound is water.

10. Process according to claim 1, said carboxylic acid derivative being an alkyl or aryl carboxylic acid derivative.

11. Process according to claim 10, said alkyl or aryl carboxylic acid derivative being a carboxylic acid ester.

12. Process according to claim 1, said carboxylic acid derivative being an ester.

13. Process according to claim 1, wherein said compound is said HS compound.

14. Process according to claim 13, wherein said HS compound is hydrogen sulfide.

15. Process according to claim 1, wherein said compound is said hydrogen halide.

16. Process according to claim 15, wherein said hydrogen halide is hydrogen chloride.

17. Process of claim 1, wherein said carboxylic acid derivative is an alkyl ester, a nitrile, a phenyl ester or the diethyl amide.

18. Process of claim 1, wherein the carboxylic acid and derivative is the diethyl amide, the phenyl ester, the $-CH_2C(CH_3)_3$ ester, the methyl ester or the nitrile.

19. Process of claim 1, wherein said compound is water.

* * * * *

UNITED STATES PATENT AND TRADEMARK OFFICE
CERTIFICATE OF CORRECTION

PATENT NO. : 4,005,132
DATED : January 25, 1977
INVENTOR(S) : Roland Köster and Hans Bellut It is certified that error appears in the above—identified patent and that said Letters Patent are hereby corrected as shown below:

Column 7, line 18, "$10^-$" should be --$10^{-3}$--.

Signed and Sealed this

Third Day of May 1977

[SEAL]

Attest:

RUTH C. MASON
*Attesting Officer*

C. MARSHALL DANN
*Commissioner of Patents and Trademarks*